(12) United States Patent
Bromenshenk et al.

(10) Patent No.: US 6,910,941 B2
(45) Date of Patent: Jun. 28, 2005

(54) HONEY BEE MONITORING SYSTEM FOR MONITORING BEE COLONIES IN A HIVE

(75) Inventors: Jerry Bromenshenk, Missoula, MT (US); Robert A. Seccomb, Missoula, MT (US); Steven D. Rice, Victor, MT (US); Robert T. Etter, Missoula, MT (US)

(73) Assignee: The University of Montana, Missoula, MT (US)

( * ) Notice: Subject to any disclaimer, the term of this patent is extended or adjusted under 35 U.S.C. 154(b) by 0 days.

(21) Appl. No.: 10/631,175

(22) Filed: Jul. 30, 2003

(65) Prior Publication Data

US 2004/0077290 A1 Apr. 22, 2004

Related U.S. Application Data

(60) Provisional application No. 60/399,616, filed on Jul. 30, 2002, and provisional application No. 60/400,034, filed on Jul. 30, 2002.

(51) Int. Cl.[7] .............................................. A01K 47/06
(52) U.S. Cl. ............................................. 449/3; 449/20
(58) Field of Search ............................. 449/1, 2, 3, 20; 340/573.2, 690, 870.17

(56) References Cited

U.S. PATENT DOCUMENTS

| | | | |
|---|---|---|---|
| 4,875,042 A | * 10/1989 | Oku et al. ............. | 340/870.17 |
| 5,015,212 A | * 5/1991 | Spangler et al. ............... | 449/2 |
| 5,517,201 A | * 5/1996 | Thompson, Jr. ............ | 342/417 |
| 6,067,030 A | * 5/2000 | Burnett et al. ......... | 340/870.05 |
| 6,266,579 B1 | * 7/2001 | Baraty ........................ | 700/275 |
| 2003/0167124 A1 | * 9/2003 | Bowden ........................ | 702/2 |

FOREIGN PATENT DOCUMENTS

| | | |
|---|---|---|
| DE | 29608 489 U 1 | 8/1996 |
| FR | 2 820 536 A | 8/2002 |

OTHER PUBLICATIONS

Spangler, Hayward G., Photoelectrical Counting of Outgoing and Incoming Honey Bees, J. Econ. Entomol., 1969, 62: 1183–1184.
Struye, MH, Microprocessor–controlled monitoring of honeybee flight activities at the hive entrance, Apidologie, 1994, 25: 384–395.
Database WPI, XP002264198, Jul. 9, 1995, Section PQ, Week 199613, Derwent Publications Ltd., London, GB.
Database WPI, XP002264199, Jul. 20, 1998, Section PQ, Week 199836, Derwent Publications Ltd., London, GB.
Database WPI, XP002264200, Jun. 15, 1992, Section PQ, Week 199320, Derwent Publications Ltd., London, GB.

* cited by examiner

Primary Examiner—Robert P. Swiatek
(74) Attorney, Agent, or Firm—Saliwanchik, Lloyd & Saliwanchik

(57) ABSTRACT

An integrated bee monitoring system for monitoring bee colonies in a hive has a central microprocessor, at least two input transducers and at least two output signals. Input transducers include sensors which report the status of the colonies including colony weight, temperature, and relative humidity. A bee counter can also be included in the system to indicate colony activity. A bee counter is disclosed which uses an amplifying, multiplexer hysteresis and debounce circuitry to enable rapid and accurate polling of a single passageway. Information collected can be retrieved by readout or liquid crystal display. Alternatively, information ca be retrieved by telephone line or wireless communications. The bee monitoring system also can remotely control peripheral devices such as feeders or chemical samplers.

9 Claims, 3 Drawing Sheets

```
Write to out port to select counter bank
WrPortI (PBDR, &PBDRShadow, bank<<6);

count = RdPortI (PADR);

for (i=0; i<4; i++) {
    j = bank*4 + i;
    temp = (count>> (2*i)) & 0x03;  // get this channel's bits
    if ((channel [j] & 0x03) != temp)
    {
        if ((((channel [j] & 0x03) == 0x00) && ((temp<<2) == (channel [j] & 0x0C)))  // bulking bee
            // pop the stack
            channel [j] = (channel [j] >> 2) | 0xC0;
        else
        {
            // analysis
            if ((temp == 0x03) && (channel [j] == 0xD2)) {in++; timeins [period] ++;}   // we got an in!
            if ((temp == 0x03) && (channel [j] == 0xE1)) {out++; timeouts [period] ++;} // we got an out!
            // push new value onto "stack"
            channel [j] = ((channel [j] & 0x3F) << 2) | temp;
            less rigorous method, for fast bees and slow detectors
            if (channel [j] == 0xD3) {in++; timeins [period] ++;}
            if (channel [j] == 0xE3) {out++; timeouts [period]++;}
        }
    }
} // end for i loop
} // end bank loop
looper++;    // cycle counter
} // end costate
```

FIG. 3

HONEY BEE MONITORING SYSTEM FOR MONITORING BEE COLONIES IN A HIVE

CROSS-REFERENCE TO RELATED APPLICATIONS

This application claims the benefits of U.S. Provisional Patent Application Nos. 60/399,616, filed Jul. 30, 2002 and 60/400,034, filed Jul. 30, 2002. The disclosures of each of these applications are hereby incorporated by reference in their entirety, including all figures, tables and drawings.

The subject invention was made with government support under a research project supported by the Defense Advanced Research Projects Agency (DARPA), Grant No. N66001-98-8630, Amendment #P0005 and the Space and Naval System Center. The government has certain rights in this invention.

BACKGROUND OF THE INVENTION

There are approximately 2.5 million honey bee colonies in the United States. These colonies increase crop yields by an estimated $12–14 billion. Honey bee colonies are susceptible to poisoning from pesticides and pollutants and thus the hives must be monitored daily. Further, pollination efficiency can be assessed and regulated by monitoring hive welfare.

Using current technologies, routine management of bee colonies requires time consuming on-site visual inspection of each hive. Although this may not be a problem for a beekeeper with a few hives, it becomes a major cost factor to a beekeeper who makes most or all of his or her living by managing hundreds to tens of thousands of hives. In addition, because many beekeepers practice migratory beekeeping, their colonies may be distributed over large geographic areas. For example, in the United States, it is not uncommon for a migratory beekeeper to move and deploy hives all the way from California to Minnesota, or from Florida to the Dakotas.

Various contrivances have been built to monitor beehive activity, consisting of an assortment of mechanical systems, hydraulic devices, heat sensors and oscillating cylinders, weight systems, and counting systems. Virtually all of these devices are highly imprecise and require constant maintenance. Simple sensors such as temperature probes are sometimes used to monitor colonies. Simple spring-mounted or electronic balance scales are used to weight hives. In 1969, Spangler published the details of a photoelectric counting device for hives to monitor the number of outgoing and incoming bees (J. Econs. Entomol., 62, 1183–1184). Struye et al. described a microprocessor-controlled monitoring unit to record honey bee flight at the hive in 1994 (Apidologie 25, 184–195). A group of bee counters named BeeScan, Apiscan, and Bumblescan sold by Lowland Electronics bvba, Belgium (BE101105A6) were developed using Struye's work. The counters incorporated two infra-red detectors on a single chip, separated by a microgap. The counters can resolve a separation of 1 mm between bees which reduces the chance of miss counting bees as they move head to tail through the counter. These counters, have an on-hive microprocessor and liquid crystal display (LCD) but they simply count bees. Programming the microprocessor is laborious and the unit is costly. Data from the BeeScan must be collected at the hive or can be downloaded to a portable computer. Although the BeeScan must be collected at the hive or can be downloaded to a portable computer. Although the BeeScan units are reliable, data from the counters can not be downloaded in continuous mode or ported to a communications network. In addition, the counter pools all data from all of the 32 ingress/egress passageways, making it impossible to separate and compare sequential signals from each passageway.

Better bee management increases honey production, reduces bee loss and improves pollination efficacy. Honey bee colonies can be used to assess environmental health, and more recently are being used to locate harmful materials, including chemicals and biological warfare agents, as well as devices such as land mines. A bee monitoring system can be used to study the toxic and sub-lethal (behavioral) effects of exposure to pesticide in the field revolutionizing pesticide investigations as well as providing a much improved method for assessing the hazard of new formulations as part of the required EPA label registration process. An integrated bee monitoring system would allow remote monitoring of honey bee activity and colony welfare as well as provide remote control of sampling devices or instruments for the collection of agents of harm. No such system currently exists.

SUMMARY

The bee monitoring system of the subject invention allows honey bee population dynamics to be monitored, including flight activity, colony brood nest temperatures and colony weight gain or loss, at the hive. The bee monitoring system also controls sampling devices and hive-mounted chemical and biological analysis instruments. Colony condition can be monitored and managed using the subject system at the hive by means of a liquid crystal display (LCD) readout, or using a handheld computer in the beeyard, or at a distance using telephone line, cell phone, satellite, or other wireless communications. In the same manner, environmental sampling systems can be switched on and off based on information feedback at the hive or by a clock function. Alternatively, the systems of the subject invention can be remotely controlled through a communications network.

The bee monitoring system of the subject invention is a comprehensive system that combines sensor and data input, as well as communication and display output and controls remote analytical and sampling devices. A microprocessor controller coordinates the multiple input and output signals. A variety of sensors can be associated with the microprocessor controller that input information as to the colonies' condition. For example, weight sensors monitor honey production. Likewise, temperature, humidity and activity sensors as well as a global positioning system report the current status of the hive. Data can also be entered via a keyboard. Output signals are sent to a monitor or LCD. Additionally, data from the hive can be sent off-site by telephone line or through wireless communications. Further, the system of the subject invention can be used to control peripheral devices such as feeders or chemical samplers.

The bee monitoring system of the subject invention can comprise a bee counter. A preferred embodiment of a bee counter is described which uses infra-red detectors and emitters mounted in ingress/egress passageways. Low cost, off-the-shelf emitters and detectors are combined with a microproccessor to separate and compute sequential signals to improve resolution. The subject counter uses an amplifier that conditions and eliminates false signals, a multiplexer and sampler with the capability of looking at only one passageway at a time, a hysteresis circuit, and de-bounce circuitry to remove bounce in the switching system. The entire system enables rapid and accurate polling of the detectors, achieving a high degree of bee separation resolution via the fast timing of the counting cycles.

BRIEF DESCRIPTION OF THE DRAWINGS

FIG. 3 shows a preferred embodiment of source code for programming the microprocessor of a preferred bee counter for inclusion into the bee monitoring system of the subject invention.

DETAILED DESCRIPTION OF THE INVENTION

Figure 1:
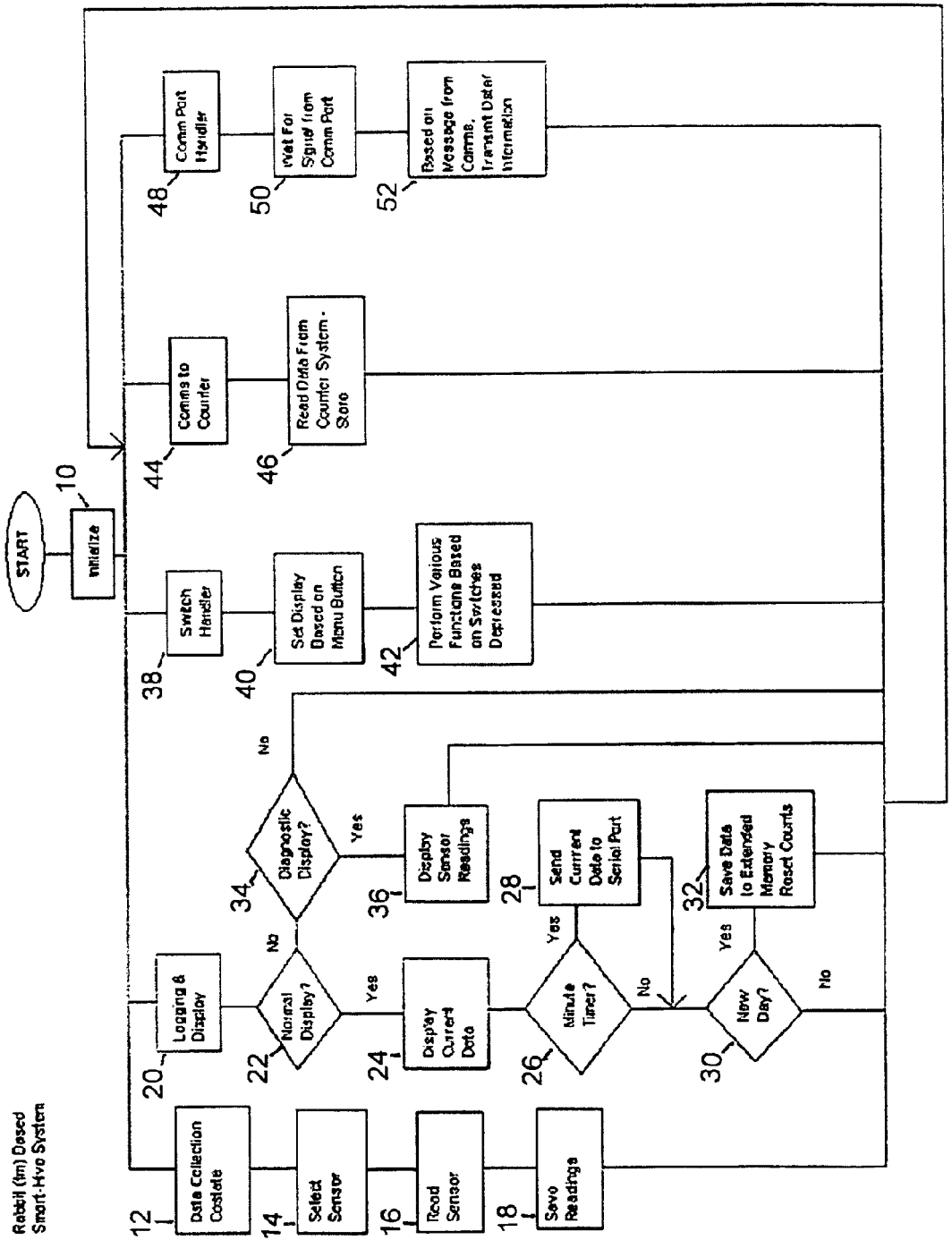
FIG. 1 shows a flow chart of a preferred embodiment of the programming of the microprocessor of the bee monitoring system of the subject invention.

The bee monitoring system of the subject invention is an integrated system which collects data from multiple sensors and devices (probes, counter), combines and processes that data at the hive, controls external devices such as sampling pumps and analytical instruments, and communicates the results via a variety of means, including real-time or near real-time delivery via the internet.

The bee monitoring system of the subject invention has an associated microprocessor and LCD display. In addition, the data acquisition and controller system interfaces with multiple sensors to control or switch on and off sampling and communications systems. In total, this resulted in a rugged, versatile, and flexible system for monitoring a diverse and numerous array of sensors (temperature, load cell, relative humidity, bee counter, and other sensors as appropriate) and for controlling other devices, including sophisticated chemical and biological sampling and/or analysis instrumentation.

The bee monitoring system of the subject invention has a microprocessor, at least two input transducers and at least two output signals. The microprocessor of the subject monitoring and control system should be reliable and be capable of handling a plurality of inputs and outputs. In a preferred embodiment, the microprocessor is a RABBIT™ 2000 microprocessor. The RABBIT™ 2000 microprocessor is flexible and easy to program. The microprocessor can be easily upgraded. Further, advantageously, this microprocessor is small and consumes little power making it ideal for incorporation into the rugged on-site instrument system of the subject invention.

The subject controller system has at least two input transducers. These input transducers can include sensors that are used to monitor the hive environment. These sensors include, but are not limited to, those that record the temperature at the hive, the weight of the hive and relative humidity. A global positioning system can assure the hives have been left undisturbed. Hive activity is monitored with a bee counter. A particularly preferred counter for incorporation into the bee monitoring system of the subject invention is described below. Data can be input into the microprocessor using a keyboard.

The bee monitoring controller system of the subject invention has at least two output signals. Data collected are output to a monitor or an LCD. Further, these data can be transmitted to a location away from the hive by communications means including wired and wireless networks. For example, a phone line provides both input and output communication with the hive. Wireless communication through a radio cell or satellite allows the bee keeper to manage the hive remotely.

The controller system of the subject invention also remotely controls analytical and sampling devices. Devices that can be controlled include, but are not limited to, pump switches, solenoids, relays and contacts for feeders, chemical pumps, chemical sampler and monitor detectors. A hive theft system could likewise be controlled from a remote location.

The central microprocessor controls and integrates the many functions of the bee monitoring system of the subject invention. One skilled in the art would know how to program the microprocessor to perform these various functions. FIG. 1 however shows a preferred embodiment of programming of a RABBIT™ 2000 microprocessor for use in the bee monitoring system of the subject invention. The program begins upon initialization [STEP 10]. The data collection costate [STEP 12] instructs the unit to select a sensor [STEP 14]. The sensor is read [STEP 16] and the reading is saved [STEP 18].

Sensor readings are logged and displayed [STEP 20]. The user must chose [STEP 22] whether a normal display is or is not desired. If a normal display is desired, current data are displayed [STEP 24]. At one minute intervals [STEP 26] the current data are sent [STEP 28] to a serial port. The timer is checked [STEP 30] to see if it is a new day. If it is a new day, the data are saved [STEP 32] to an extended memory and the counts are reset. When a normal display [STEP 22] is not desired, a diagnostic display can be chosen [STEP 34]. If a diagnostic display is chosen, the sensor reading is displayed [STEP 36].

The microprocessor controls switches for peripheral devices with a switch handler [STEP 38]. The display is set [STEP 40] based on the menu button. Various functions are performed [STEP 42] based on the switches depressed.

When a counter controlled by a microprocessor is included in the system of the subject invention, the microprocessors communicate [STEP 44] with one another. Data from the counter system is read and stored [STEP 46].

The system of the subject invention can be accessed and controlled remotely. A communication port handler [STEP 48] waits [STEP 50] for a signal from the communication port. Based on the message from the communication port, data or information will be transmitted [STEP 52]. Likewise, a message from the communication port can instruct counts to be reset or switches to be depressed.

The bee monitoring system of the subject invention preferably comprises a bee counter. A particularly preferred bee counter to be included in the subject system has transducers to detect the presence of a bee and its direction of motion. The resulting electrical signals are processed through hysteresis circuits to reduce susceptibility to noise and minor motions of the bees. Each transducer has its own conditioning circuit. Processed signals are multiplexed to allow a multitude of sensors to be routed to eight inputs of a microprocessor. The program in the microprocessor scans the transducer inputs and determines the direction of bee travel, counting the events of bee entry and exits.

Programming of counter operation and observation of accumulated data may be performed either with a pendent that switches for programming or selecting options and an alphanumeric display, or through a serial data link to a computer or communications device (modem). The signal amplifying and conditioning circuitry with de-bounce capability, has a wider potential use in non-bee related devices, such as in manufacturing.

Figure 2:
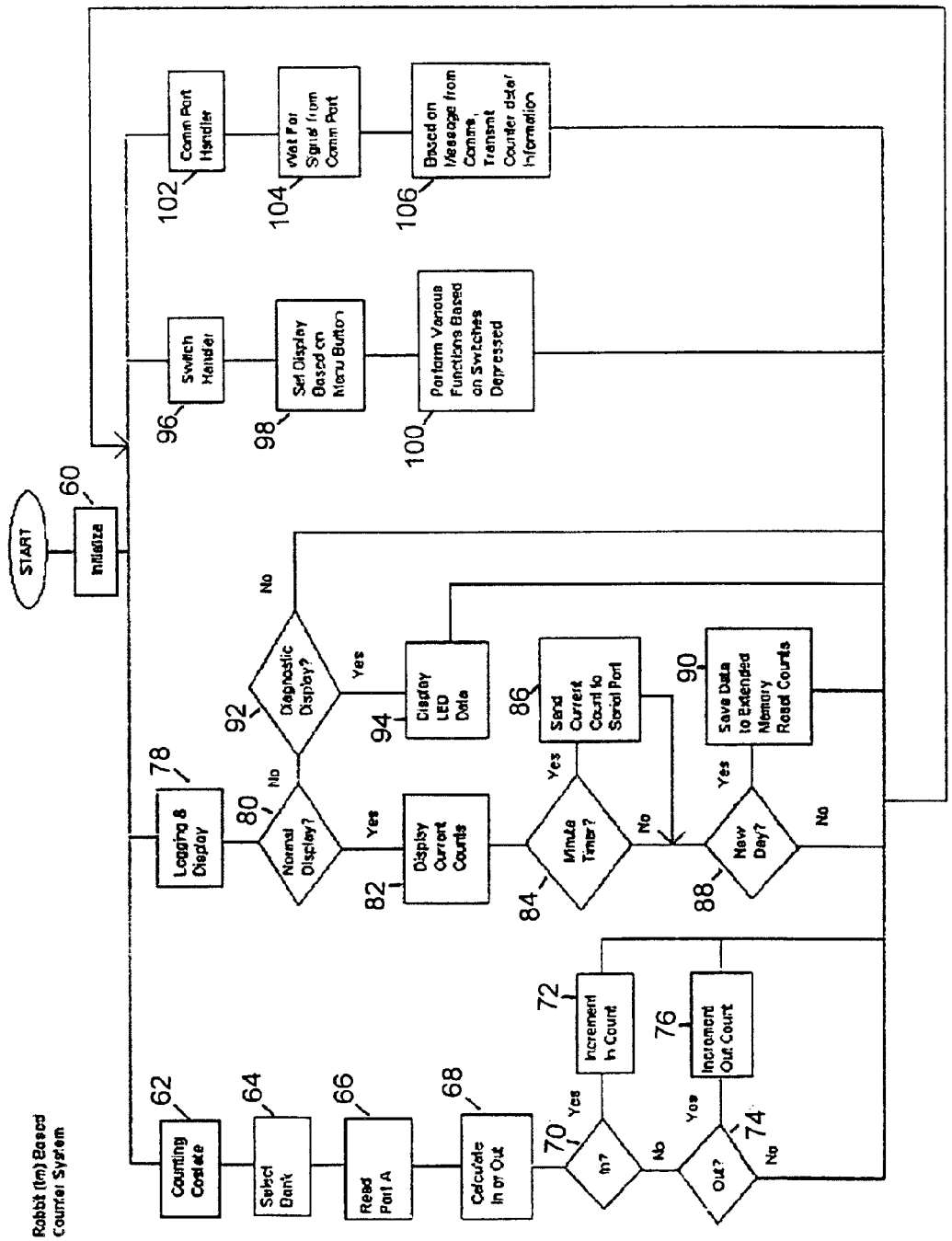
FIG. 2 shows a flow chart of a preferred embodiment of the programming of the microprocessor of a preferred bee counter for inclusion into the bee monitoring system of the subject invention.

FIG. 2 shows a preferred embodiment of programming of the microprocessor of the counter of the subject invention. Upon initialization [STEP 60], bees are countered entering and leaving the hive via a counting costate [STEP 62]. A bank is selected [STEP 64] for counting. A bank is a block of doors. For example, on a hive with 14 doors, four doors or channels would be counted at one time. This data is read [STEP 66] from the input/output (I/O) port on the microprocessor, for example port A. The number of counts in or out are calculated [STEP 68]. Source code of a particularly preferred method of calculating these counts is shown in FIG. 3. Using this code, counts are completed accurately and quickly. If the count is in [STEP 70] than it will be incremented [STEP 72] as and in count. If the count is not an in count, it is asked whether the count was an out count [STEP 74]. If yes, the count is incremented [STEP 76] as an out count. Counts are logged and displayed [STEP 78]. The user must chose [STEP 80] whether a normal display is or is not desired. If a normal display is desired, current counts are displayed [STEP 82]. At one minute intervals [STEP 84] the current counts are sent [STEP 86] to a serial port. The time is checked [STEP 88] to see if it is a new day. If it is a new day, the counts are saved [STEP 90] to an extended memory and the counts are reset. When a normal display [STEP 80] is not desired, a diagnostic display can be chosen [STEP 92]. If a diagnostic display is chosen, the raw channel data are displayed [STEP 94].

The microprocessor of the counter controls switches for peripheral devices with a switch handler [STEP 96]. The display is set [STEP 98] based on the menu button. Various functions are performed [STEP 100] based on the switches depressed.

The subject counter can be accessed and controlled remotely. A communication port handler [STEP 102] waits [STEP 104] for a signal from the communication port. Based on the message from the communication port, data or information will be transmitted [STEP 106].

It is understood that the foregoing examples are merely illustrative of the present invention. Certain modifications of the articles and/or methods employed may be made and still achieve the objectives of the invention. Such modifications are contemplated as within the scope of the claimed invention.

What is claimed is:

1. A bee monitoring system for monitoring bee colonies in a hive comprising:
    a microprocessor;
    at least two input transducers, wherein one of said at least two input transducers is a bee counter comprising; at least one set of an emitter and two detectors, the set comprising an amplifier, a hysteresis circuit and a debounce circuit; a microprocessor; and a multiplexer; and
    at least two input signals.

2. The monitoring system of claim 1, wherein said hive has a plurality of doors and said counter has a plurality of sets of emitters and detectors and said counter is capable of counting bees in a single door of the hive.

3. The monitoring system of claim 1, wherein said microprocessor comprises a single board, at least eight input transducers, at least eight output signals, at least one serial port, said microprocessor running at least at 10 megahertz, and comprising at least 64 kilobytes of random access memory.

4. The monitoring system of claim 1, wherein bees are counted as a bee passes said emitter and two detectors of said at least one set of an emitter and two detectors creating a state comprising a sequence of bits in a stack; said microprocessor comprising programming comprising the steps of;
    comparing a current state to a previous state; and based on that comparison determining;
    if said bee passed from the outside of said hive to the inside of said hive, then recording an "in" count;
    if said bee passed from the inside of said hive to the outside of said hive, then recording an "out" count; and
    if said bee did not pass said emitter and two detectors, then resetting the state.

5. A bee counter for a hive comprising:
    at least one set of an emitter and two detectors, the set comprising an amplifier, a hysteresis circuit and a debounce circuit;
    a microprocessor; and
    a multiplexer.

6. The bee counter of claim 5, wherein said hive has a plurality of doors and said counter has a plurality of sets of emitters and detectors and said counter is capable of counting bees in a single door of the hive.

7. The bee counter of claim 5, wherein said microprocessor comprises a single board, at least eight input transducers, at least eight output signals, at least one serial port, said microprocessor running at least at 10 megahertz, and comprising at least 64 kilobytes of random access memory.

8. The bee counter of claim 5, wherein bees are counted as a bee passes said emitter and two detectors of said at least one set of an emitter and two detectors creating a state comprising a sequence of bits in a stack; said microprocessor comprising programming comprising the steps of;
    comparing a current state to a previous state; and based on that comparison determining;
    if said bee passed from the outside of said hive to the inside of said hive, then recording an "in" count;
    if said bee passed from the inside of said hive to the outside of said hive, then recording an "out" count; and
    if said bee did not pass said emitter and two detectors, then resetting the state.

9. A bee monitoring system for monitoring bee colonies in a hive comprising:
    a microprocessor;
    at least eight input transducers selected from the group consisting of a temperature sensor, a scale, a humidity sensor, and a global positioning system;
    a counter comprising at least one set of an emitter and two detectors, the set comprising an amplifier, a hysterisis circuit, and a de-bounce circuit; a microprocessor; and a multiplexer, wherein the hive comprises a plurality of doors and the counter comprises a plurality of emitters and a plurality of detectors and the counter is capable of counting bees in a single door of the hive; and
    at least two output signals, wherein the output signals are transmitted by a method selected from the group consisting of telephone line, radio, and satellite and wherein the output signals are capable of controlling remote devices.

* * * * *